(12) United States Patent
Pettibone et al.

(10) Patent No.: US 7,133,119 B1
(45) Date of Patent: Nov. 7, 2006

(54) SYSTEMS FOR SIMULATING HIGH NA AND POLARIZATION EFFECTS IN AERIAL IMAGES

(75) Inventors: Don Pettibone, San Jose, CA (US); Stan Stokowski, Danville, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 343 days.

(21) Appl. No.: 10/736,409

(22) Filed: Dec. 15, 2003

Related U.S. Application Data

(60) Provisional application No. 60/434,145, filed on Dec. 17, 2002.

(51) Int. Cl.
- *G03B 27/72* (2006.01)
- *G03B 27/52* (2006.01)
- *G03B 27/54* (2006.01)
- *G01N 21/00* (2006.01)

(52) U.S. Cl. ............... 355/71; 355/55; 355/67; 356/237.1

(58) Field of Classification Search ........ 356/491, 356/237.1, 237.2, 237.4, 237.5; 355/55, 355/53, 67, 71, 68; 430/5; 250/548
See application file for complete search history.

(56) References Cited

U.S. PATENT DOCUMENTS

| | | | |
|---|---|---|---|
| 4,247,203 A | 1/1981 | Levy et al. | |
| 4,347,001 A | 8/1982 | Levy et al. | |
| 4,378,159 A | 3/1983 | Galbraith | |
| 4,448,532 A | 5/1984 | Joseph et al. | |
| 4,532,650 A | 7/1985 | Wihl et al. | |
| 4,555,798 A | 11/1985 | Broadbent, Jr. et al. | |
| 4,579,455 A | 4/1986 | Levy et al. | |
| 4,633,504 A | 12/1986 | Wihl | |
| 4,641,967 A | 2/1987 | Pecen | |
| 4,758,094 A | 7/1988 | Wihl et al. | |
| 4,766,324 A | 8/1988 | Saadat et al. | |
| 4,805,123 A | 2/1989 | Specht et al. | |
| 4,845,558 A | 7/1989 | Tsai et al. | |
| 4,877,326 A | 10/1989 | Chadwick et al. | |

(Continued)

FOREIGN PATENT DOCUMENTS

EP    1 061 358    12/2000

(Continued)

OTHER PUBLICATIONS

Pistor, "Electromagnetic Simulation and Modeling with Applications in Lithography," 2001, p. 56.

(Continued)

*Primary Examiner*—Gregory J. Toatley, Jr.
*Assistant Examiner*—Marissa J Detschel
(74) *Attorney, Agent, or Firm*—Ann Marie Mewherter; Daffer McDaniel, LLP

(57) ABSTRACT

Reticle inspection systems are provided. One embodiment includes an optical subsystem configured to produce an aerial image of a reticle by simulating dose as a function of position that would be projected into a resist by an exposure system such that the aerial image is substantially equivalent to an image of the reticle that would be projected into the resist by the exposure system. Another embodiment includes an optical subsystem configured to alter one or more properties of light such as polarization transmitted by a reticle and to project the light onto a detector. An additional embodiment includes an optical subsystem configured to form an intermediate aerial image of a reticle at a numerical aperture approximately equal to a numerical aperture at which an exposure system projects an image of the reticle into a resist and to project the intermediate aerial image onto a detector.

21 Claims, 4 Drawing Sheets

U.S. PATENT DOCUMENTS

| | | |
|---|---|---|
| 4,899,055 A | 2/1990 | Adams |
| 4,926,489 A | 5/1990 | Danielson et al. |
| 5,189,481 A | 2/1993 | Jann et al. |
| 5,365,371 A | 11/1994 | Kamon |
| 5,559,583 A | 9/1996 | Tanabe |
| 5,563,702 A | 10/1996 | Emery et al. |
| 5,572,598 A | 11/1996 | Wihl et al. |
| 5,680,588 A | 10/1997 | Gortych et al. |
| 5,737,072 A | 4/1998 | Emery et al. |
| 5,889,593 A | 3/1999 | Bareket |
| 6,052,478 A | 4/2000 | Wihl et al. |
| 6,076,465 A | 6/2000 | Vacca et al. |
| 6,122,046 A | 9/2000 | Almogy |
| 6,137,570 A | 10/2000 | Chuang et al. |
| 6,141,038 A | 10/2000 | Young et al. |
| 6,175,645 B1 | 1/2001 | Elyasaf et al. |
| 6,268,093 B1 | 7/2001 | Kenan et al. |
| 6,282,309 B1 | 8/2001 | Emery |
| 6,363,166 B1 | 3/2002 | Wihl et al. |
| 6,392,800 B1 | 5/2002 | Schuster |
| 6,404,482 B1 | 6/2002 | Shiraishi |
| 6,614,520 B1 | 9/2003 | Bareket et al. |
| 6,636,301 B1 | 10/2003 | Kvamme et al. |
| 6,665,052 B1 * | 12/2003 | Sato .......................... 355/71 |

FOREIGN PATENT DOCUMENTS

| | | |
|---|---|---|
| EP | 1 061 571 | 12/2000 |
| EP | 1 069 609 | 1/2001 |
| WO | 99/38002 | 7/1999 |
| WO | 99/59200 | 11/1999 |

OTHER PUBLICATIONS

Smith et al., "Challenges in high NA, polarization, and photoresists," Proceedings of SPIE vol. 4691, 2002, pp. 11-24.

* cited by examiner

REPLACEMENT SHEET
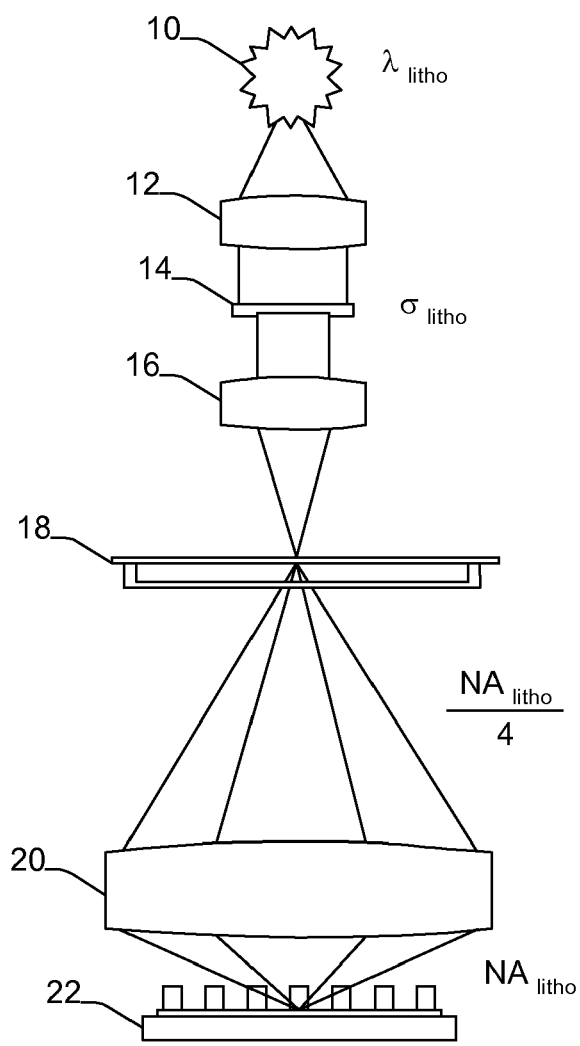
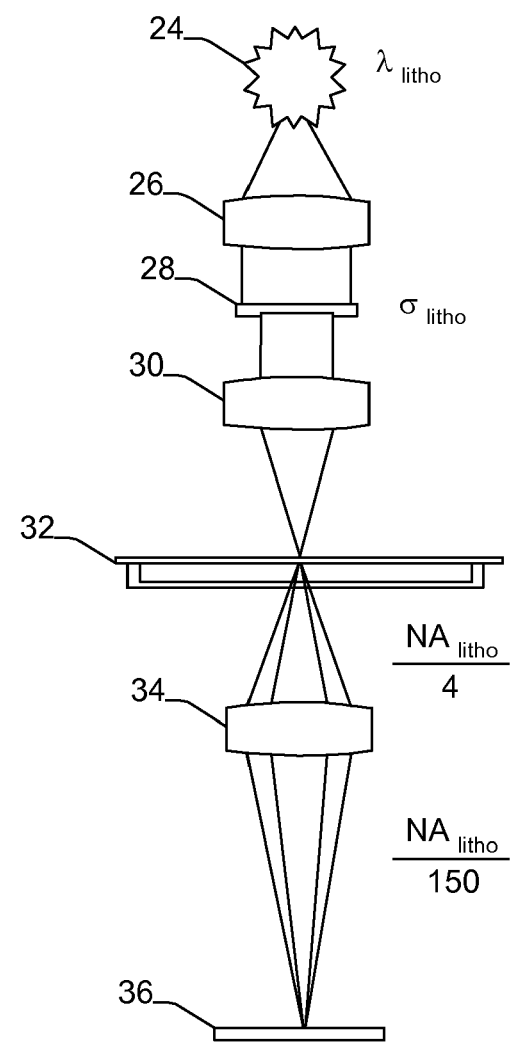
Fig. 1
(Related Art)
Fig. 2
(Related Art)

SYSTEMS FOR SIMULATING HIGH NA AND POLARIZATION EFFECTS IN AERIAL IMAGES

PRIORITY CLAIM

This application claims priority to U.S. Provisional Application No. 60/434,145 entitled "Systems for Simulating High NA and Polarization Effects in Aerial Images," filed Dec. 17, 2002.

BACKGROUND OF THE INVENTION

1. Field of the Invention

This invention generally relates to reticle inspection systems. Certain embodiments relate to systems for inspecting reticles using aerial imaging and simulating high NA and polarization effects in the aerial images.

2. Description of the Related Art

Semiconductor fabrication processes typically involve a number of lithography steps to form various features and multiple levels of a semiconductor device. Lithography involves transferring a pattern to a resist formed on a semiconductor substrate, which may be commonly referred to as a wafer. A reticle, or a mask, may be disposed above the resist and may have substantially transparent regions and substantially opaque regions configured in a pattern that may be transferred to the resist. As such, substantially opaque regions of the reticle may protect underlying regions of the resist from exposure to an energy source. The resist may, therefore, be patterned by selectively exposing regions of the resist to an energy source such as ultraviolet light, a beam of electrons, or an x-ray source. The patterned resist may then be used to mask underlying layers in subsequent semiconductor fabrication processes such as ion implantation and etch. Therefore, a resist may substantially inhibit an underlying layer such as a dielectric material or the semiconductor substrate from implantation of ions or removal by etch.

There are several types of reticles that are commercially available. For example, a reticle may be either a clear-field reticle or a dark-field reticle. A clear-field reticle has field or background areas that are opaque, and a dark-field reticle has field or background areas that are transparent. In addition, a binary reticle is a reticle having a patterned area that is either transparent or opaque. Binary reticles are different from phase-shift masks (PSM) that may include films that only partially transmit light, and these reticles may be commonly referred to as halftone or embedded reticles. If a phase-shifting material is placed on alternating clear spaces of a reticle, the reticle is referred to as an alternating PSM, an ALT PSM, or even a Levenson PSM. If a phase-shifting material is applied to arbitrary layout patterns, the reticle is referred to as an attenuated or halftone PSM, which may be fabricated by replacing the opaque material with a partially transmissive or "halftone" film. A ternary attenuated PSM is an attenuated PSM that includes CR features. Each of the reticles described above may also include a pellicle, which is an optically transparent membrane that seals off the reticle surface from airborne particulates and other forms of contamination.

A process for manufacturing a reticle is similar to a wafer patterning process. For example, the goal of reticle manufacturing is forming a pattern in an opaque material such as a relatively thin chrome layer on a substantially transparent substrate such as glass. In addition, other appropriate opaque materials that may be used for reticle manufacturing include, but are not limited to, chromium, chromium oxide, and chromium nitride. Appropriate thicknesses for chrome layers may be approximately 1000 Å and may be deposited upon a glass substrate by sputtering. Additional appropriate transparent materials that may be used for reticle manufacturing include borosilicate glass or fused-silica ($SiO_2$, "quartz"), which have good dimensional stability and transmission properties for wavelengths of exposure systems. Additional materials may also be used for reticle manufacturing. For example, a film underlying an opaque material may act as an adhesion layer. Such an adhesion layer may include, for example, a mixture of chromium, nitrogen, and oxide. In addition, a film formed on top of the opaque material may act as an anti-reflective layer. An appropriate anti-reflective layer may be formed of, for example, a relatively thin layer of $Cr_2O_3$.

Reticle manufacturing may include a number of different steps such as pattern generation, which may include moving a glass substrate having a chrome layer and a resist layer formed thereon under a light source as shutters are moved and opened to allow precisely shaped patterns of light to shine into the resist thereby creating the desired pattern. Since the patterns generated by an integrated circuit designer for each level are generally polygons, these patterns are decomposed into rectangles. The reticle pattern is transferred to the resist-covered reticle blank by a step-and-repeat process to create a master plate. The master plate is used to create multiple working reticle plates in a contact printer. The contact printer brings the master into contact with a resist-covered reticle blank and has an ultraviolet light source for transferring the image to the resist on the reticle blank.

Alternatively, reticles may be made with lasers or e-beam direct write exposure. Laser exposure allows the use of standard optical resists and is faster than e-beam direct write exposure. In addition, laser systems are also less expensive to purchase and operate. Direct write laser sources are turned on and off with an acousto-optical modulator (AOM). An example of a commercially available direct write laser system is the ALTA 3000® laser writer available from ETEC Systems, Inc., Hayward, Calif. Direct write e-beam systems are often used to manufacture complex reticles since they produce finer line resolution than laser systems. In addition, direct write e-beam systems can also write larger die sizes than laser systems. Examples of commercially available direct write e-beam systems include the MEBES 4500 and 5000 systems available from ETEC Systems, Inc.

After the exposure steps, the reticle is processed through development, inspection, etch, strip, and inspection steps to transfer the pattern into the opaque material. Defects in reticles are a source of yield reduction in integrated circuit manufacturing. Therefore, inspection of a reticle is a critical step in the reticle manufacturing process. As minimum pattern sizes shrink and integrated circuits are designed with higher device densities, defects that were once tolerable may no longer be acceptable. For example, a single defect may be repeated in each die in stepper systems and may kill every die in single-die reduction reticles. In addition, VLSI and ULSI-level integrated circuit manufacturing require substantially defect-free and dimensionally perfect reticles due to the critical dimension (CD) budget of such manufacturing. For example, the overall CD budget for such integrated circuits may be approximately 10% or better thereby resulting in a CD budget for a reticle with about a 4% error margin.

Defects may be a result of incorrect designing of the reticle pattern and/or flaws introduced into the patterns during the pattern generation process. Even if the design is correct, and the pattern generation process is performed satisfactorily, defects in the reticle may be generated by the reticle fabrication process as well as during subsequent processing and handling. In addition to the many potential causes of defects, there are also many different types of defects. For example, bubbles, scratches, pits, and fractures may be a result of a faulty raw glass substrate. Defects in the opaque material may include particulate inclusions in the material, pinholes or voids in the material surface, and invisible chemical anomalies such as nitrides or carbides that may lead to erratic local etching and undesired patterns. Defects such as voids in the resist layer may produce pinholes that may lead to chrome spots. In addition, localized characteristics in the resist may also produced variations in characteristics of the resist such as resist solubility across the reticle substrate. Particulate matter may also be introduced to the reticle during processing and/or handling of the reticle. Defects that may result in inoperative devices or which would cause a die to be rejected at final inspection are commonly referred to as "fatal" or "killer" defects, while other may be commonly referred to as "nonfatal" defects.

SUMMARY OF THE INVENTION

An embodiment of the present invention relates to a reticle inspection system. The reticle inspection system includes an optical subsystem. The optical subsystem is configured to produce an aerial image of a reticle by simulating dose as a function of position that would be projected into a resist by an exposure system. In this manner, the aerial image is substantially equivalent to an image of the reticle that would be projected into the resist by the exposure system. In one embodiment, simulating dose as a function of position includes altering the aerial image to correct for differences between a numerical aperture at which the exposure system projects the aerial image into the resist and a numerical aperture at which the optical subsystem produces the aerial image. In another embodiment, the optical subsystem includes a detector configured to produce the aerial image. In one such embodiment, simulating dose as a function of position includes forming an intermediate aerial image at a numerical aperture approximately equal to a numerical aperture at which the exposure system projects the image into the resist and projecting the intermediate image onto the detector. In another embodiment, simulating dose as a function of position includes altering interference of electric fields of p-polarized light at an image plane of the optical subsystem such that the interference is approximately equivalent to an interference of the electric fields of the p-polarized light in photoresist.

In some embodiments, simulating dose as a function of position includes altering an intensity of p-polarized light in the aerial image such that the intensity is approximately equal to an intensity of the p-polarized light in the image projected into the resist by the exposure system. In addition or alternatively, simulating dose as a function of position includes altering an intensity of s-polarized light in the aerial image such that the intensity is approximately equal to an intensity of the s-polarized light in the image projected into the resist by the exposure system.

In one embodiment, the optical subsystem includes an optical filter configured to alter polarization characteristics of light in the aerial image such that the polarization characteristics are substantially equivalent to polarization characteristics of light in the image projected into the resist by the exposure system. In another embodiment, the optical subsystem is configured to illuminate the reticle with light having polarization characteristics substantially equivalent to polarization characteristics of light projected onto the reticle by the exposure system.

In an additional embodiment, the optical subsystem may include a spatial filter. The spatial filter may include two equivalent objective lenses and an optical filter disposed at a focal point between the two equivalent objective lenses. In another embodiment, the optical subsystem includes a spatial filter and a detector. In one such embodiment, the spatial filter includes a first equivalent objective lens configured to form an intermediate aerial image of the reticle. The spatial filter may also include an optical filter disposed at a back focal plane of the first equivalent objective lens. In addition, the spatial filter may include a second equivalent objective lens configured to project the intermediate aerial image onto the detector.

In some embodiments, the optical subsystem may be configured to produce an aerial image that is substantially equivalent to an image of the resist that would be projected into the resist. For example, in one embodiment, simulating dose as a function of position may include altering the aerial image to simulate refraction and/or transmission of p-polarized light and/or s-polarized light in the resist. In one such embodiment, the optical subsystem includes an optical filter placed in an image plane of the optical subsystem. Transmission characteristics of the optical filter, at an operating wavelength of the exposure system, may be selected to substantially match filter characteristics of the resist, at the operating wavelength.

In yet another embodiment, the system also includes a processor configured to detect defects on the reticle by analyzing the aerial image. A substantial portion of the defects may include defects that would be printed by the exposure system. The reticle inspection system may be further configured as described herein.

Another embodiment of a reticle inspection system includes an optical subsystem configured to alter one or more properties of light transmitted by a reticle. In one embodiment, the one or more properties include interference of electric fields of p-polarized light at an image plane of the optical subsystem. In another embodiment, the one or more properties include an intensity of p-polarized light transmitted by the reticle. In an additional embodiment, the one or more properties include an intensity of s-polarized light transmitted by the reticle. The optical subsystem may also be configured to project the light onto a detector. The detector may be configured to produce an aerial image of the reticle. This embodiment of a reticle inspection system may be further configured as described herein.

An additional embodiment of a reticle inspection system includes an optical subsystem configured to form an intermediate aerial image of a reticle at a numerical aperture approximately equal to a numerical aperture at which an exposure system projects an image of the reticle into a resist. The optical subsystem may also be configured to project the intermediate aerial image onto a detector. The detector may be configured to produce an aerial image of the reticle. In one embodiment, the optical subsystem includes an optical filter configured to alter an intensity of s-polarized light and/or p-polarized light in the intermediate aerial image such that the intensity is approximately equivalent to an intensity of the s-polarized light and/or the p-polarized light in the image projected into the resist by the exposure system. The reticle inspection system may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 1 depicts a schematic diagram of a side view of an exposure system;

FIG. 2 depicts a schematic diagram of a side view of a system configured to inspect a reticle.

Figure 3:
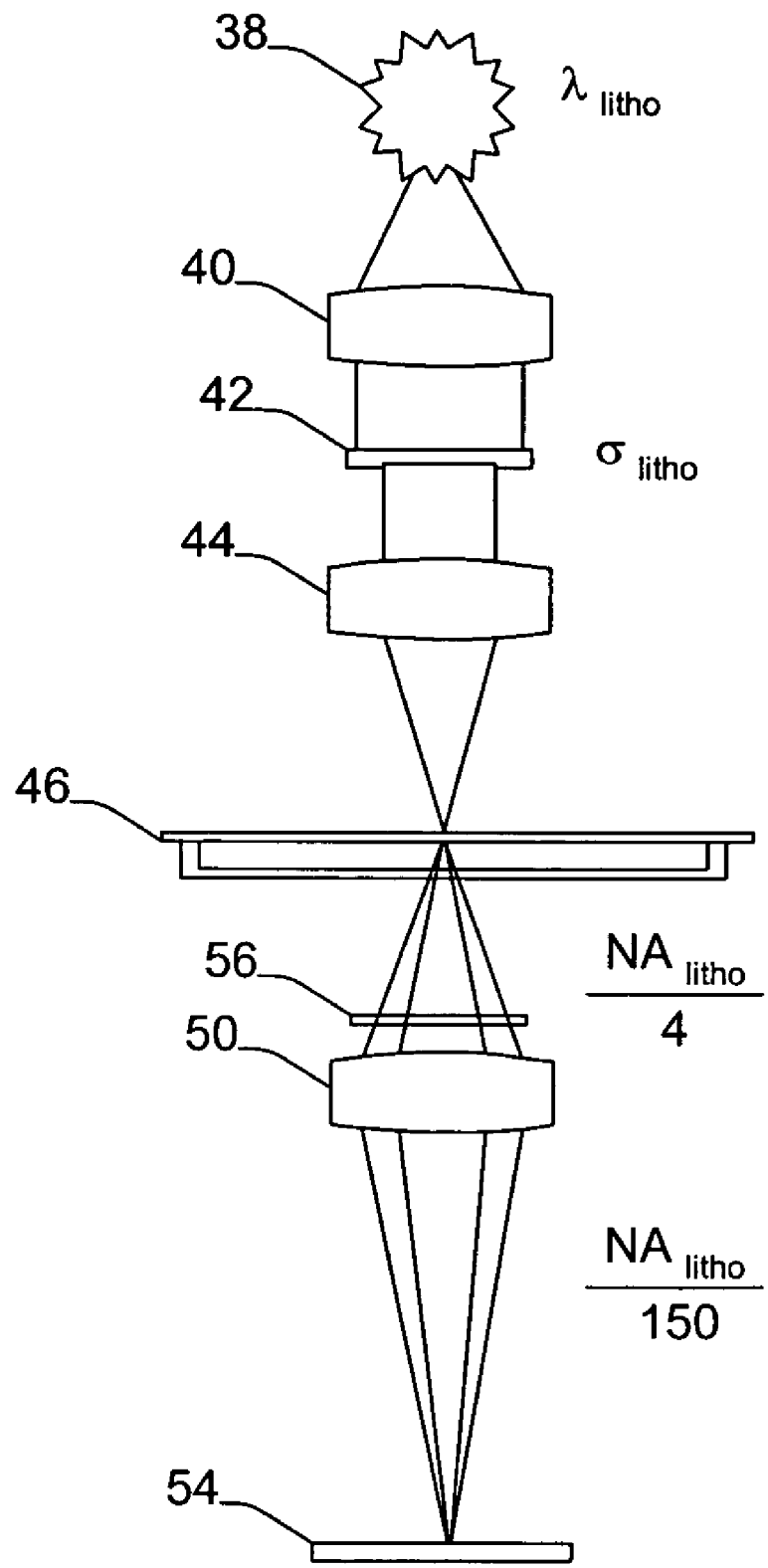
FIGS. 3–7 depict schematic diagrams of a side view of various embodiments of a reticle inspection system that includes a spatial filter.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "reticle" is used to refer to a reticle or a mask. A reticle generally includes a transparent substrate such as glass, borosilicate glass, and fused silica having a layer of opaque material formed thereon. In one example, the layer of opaque material may include chrome. A reticle may include additional materials formed under the opaque material such as an adhesion layer.

The term reticle may also refer to different types of reticles including, but not limited to, a clear-field reticle, a dark-field reticle, a binary reticle, a phase-shift mask (PSM), an alternating PSM, an attenuated or halftone PSM, and a ternary attenuated PSM, which are described in more detail above. A reticle, as described herein, may or may not include a pellicle. The term reticle may also be used to refer to a reticle that includes optical proximity correction (OPC) features. OPC features are designed to reduce distortions of an image printed using the reticle by reducing optical proximity effects. The term "optical proximity effects" generally refers to variations in lateral dimensions of printed features due to the proximity of other features on the reticle. OPC features may include, for example, sub-resolution patterns and incremental linewidth changes to a pattern (commonly referred to as "line jogs") to reduce the distortion of a feature.

As used herein, the term "exposure system" generally refers to any lithography system that prints images of a reticle onto a specimen using light. The exposure system may be a scanning projection system or a step-and-repeat system, or a "stepper." The exposure system may include any exposure system known in the art such as systems commercially available from GCA Corporation, Nikon, ASM Lithography, Canon, SVG Lithography, or Integrated Solutions, Inc.

Turning now to the drawings, FIG. 1 illustrates a side view of an exposure system. It is noted that FIGS. 1–7 are not drawn to scale. It is also noted that FIGS. 1–7 are not drawn to the same scale. The exposure system includes light source 10. Light source 10 may include, for example, a mercury lamp or an excimer laser. The light source may be configured to emit light having a selected wavelength. For example, the light source may be configured to emit monochromatic light of the selected wavelength. Alternatively, a broadband light source may be coupled to a spectral filter, which is configured to transmit only the selected wavelength. Examples of appropriate wavelengths include 365 nm, 248 nm, 193 nm, and 157 nm. Light from light source 10 may pass through homogenizer 12. Homogenizer 12 may be configured to reduce speckle of the light from the light source. The light may then pass through aperture 14. Aperture 14 may have an adjustable numerical aperture as described herein. Light from aperture 14 passes through condenser lens 16.

Light exiting condenser lens 16 illuminates reticle 18, which may be disposed on a stage (not shown). Light transmitted by reticle 18 may be collected by objective lens 20. Objective lens 20 may project an image of the reticle onto wafer 22, which may also be disposed upon a stage (not shown). The wafer may include one or more layers formed on a semiconductor substrate. The one or more layers include a resist and optionally another layer such as a top anti-reflective coating, a bottom anti-reflective coating, and dielectric or conductive layers. The exposure system may include a number of other components that are not described herein, but which are known in the art such as a fly's eye lens, a reticle blind, additional lenses, and reflective components.

The exposure system may be configured to print an image of reticle 18 on wafer 22 using a set of exposure conditions. The set of exposure conditions may include a selected wavelength of illumination, $\lambda_{litho}$, a partial coherence factor, $\sigma_{litho}$ (which may be determined as described herein), a numerical aperture on the wafer side (the image plane side) of the exposure system, $NA_{litho}$, and polarization characteristics of the light projected onto a reticle or wafer. The wavelength of illumination may include any of the wavelengths described herein. The wavelength of the illumination of an exposure system is generally fixed. In some exposure systems, the NA and the polarization characteristics are also fixed while the partial coherence factor may be altered depending upon, for example, the type, the lateral dimension, and the spatial frequency of features that are being printed. In other exposure systems, the NA and the partial coherence factor may be altered.

An increasing number of exposure systems are "high NA" systems due to the increasing demands for greater resolution. The term "high NA" is used herein to refer to a numerical aperture on the wafer side of an exposure system ("$NA_{litho}$") of greater than about 0.5. Currently available high NA exposure systems may have an $NA_{litho}$ of, for example, 0.6, 0.7, 0.75, 0.8, and 0.9. As shown in FIG. 1, the exposure system may have a numerical aperture on the reticle side (the object side) of the objective lens of about $NA_{litho}$/magnitude of reduction (i.e., $NA_{litho}$/4 for a 4× reduction system, $NA_{litho}$/5 for a 5× reduction system, etc.). Exposure systems are generally operated with a value of $\sigma_{litho}$ in a range between about 0.3 to about 0.9. The exposure system may also be configured to project light having different polarization characteristics onto a reticle or wafer than the polarization characteristics of the light emitted by the light source. For example, some exposure systems may include a half-wave plate (not shown) or another optical component configured to alter the polarization characteristics of the light emitted by the light source.

Some reticle inspection systems are configured to generate an aerial image of a reticle in an attempt to mimic an exposure system and process such that the aerial image may be used to detect "printable" defects on the reticle. One example of an aerial imaging reticle inspection system is illustrated in FIG. 2. The inspection system may be configured to generate aerial images of a reticle at conditions similar to exposure conditions of an exposure system. Therefore, some components of the inspection system may be configured to simulate these exposure conditions. For example, the inspection system may include light source 24, which emits light having a wavelength approximately equal to a wavelength of the exposure system, $\lambda_{litho}$. Light emitted by light source 24 may pass through homogenizer 26. In addition, the inspection system may include aperture 28, which may set the partial coherence factor to approximately the partial coherence factor of the exposure system, $\sigma_{litho}$. The inspection system may also include condenser lens 30, which may be configured to illuminate reticle 32.

The inspection system may have a numerical aperture on the reticle side of objective lens 34 that is approximately equal to the numerical aperture on the reticle side of the objective lens of the exposure system (i.e., $NA_{litho}/4$). The objective lens projects the aerial image of the reticle onto detector 36. The objective lens, however, has a numerical aperture on the detector side of about $NA_{litho}/150$. Therefore, the inspection system does not have a numerical aperture on the detector side of objective lens 34 that is approximately equal to a numerical aperture on the wafer side of the exposure system, $NA_{litho}$. As such, the inspection system forms the aerial image at a different NA than the exposure system. In this manner, an aerial image acquired by detector 36 will be substantially different than an aerial image printed by the exposure system.

For example, as the numerical aperture on a wafer side of an exposure system increases, the angles at which light is projected into a resist become more oblique. Therefore, as the numerical aperture increases, the propagation angles of the electric fields for p-polarized light may have a significant effect on an image that is printed on the resist. For example, interference between electric fields of p-polarized light in the image plane reduces as numerical aperture increases. As such, the vector sum of the electric fields of p-polarized light in the image plane will differ from the vector sum obtained at low NA, particularly with increasing numerical aperture. Therefore, as the interference between the electric fields of p-polarized light reduces, image contrast reduces. In other words, the intensity of an aerial image formed from the p-polarized light will become more uniform across the aerial image (i.e., the average difference in intensity between bright areas of the aerial image and dark areas of the aerial image will decrease). In contrast, complete interference of the electric fields of s-polarized light will exist regardless of the numerical aperture. Therefore, as the NA decreases, the image contrast may not be altered substantially due to the interference of the electric fields of s-polarized light. However, an aerial image that is projected into a resist is generally a sum of the images formed separately with p-polarized light and s-polarized light. Consequently, the aerial image that is projected into a resist depends on both aerial images.

As described above, conventional aerial imaging reticle inspection systems do not form aerial images of a reticle at the numerical aperture on the wafer side of the exposure system. For example, conventional aerial imaging reticle inspection systems form aerial images of a reticle at relatively high magnification (i.e., as shown in FIG. 2). Consequently, the vector sum of the electric fields of p-polarized light in the image plane of the inspection system will be substantially different than the vector sum of the electric fields of p-polarized light in the image plane of an exposure system. For example, in general, such an inspection system will have better cancellation of the electric fields of p-polarized light due to the less oblique angles at which the aerial image is formed. Therefore, a conventional aerial imaging reticle inspection system will generally over-predict the image contrast in an aerial image of the reticle (i.e., the inspection system predicts that the aerial image will have better image contrast that that which will be printed by an exposure system).

It also is important to note that conventional aerial imaging reticle inspection systems form aerial images of a reticle that would be printed in air. Therefore, conventional aerial imaging reticle inspection systems do not accurately predict aerial images of a reticle that will be printed into a resist. For example, such systems do not account for variation in the aerial image due to effects such as reflection of s-polarized light and/or p-polarized light from an upper surface of a resist. For example, s-polarized light and p-polarized light will be separately reflected from an upper surface of a resist in different amounts. The amount of s- and p-polarized light that is reflected from the resist depends on a number of factors such as the numerical aperture (or angle at which the light is projected onto the upper surface of the resist) resist optical properties and thickness and wavelength of light. As the incidence angle increases, the amount of s-polarized light that is reflected from the upper surface of the resist increases dramatically, which results in the decrease in dose into the film. In addition, the amount of p-polarized light that is reflected from the upper surface of the resist decreases slightly as the incidence angle increases.

It is believed that the above discrepancies between inspection systems and exposure systems, in large part, cause the inaccuracies in the aerial images of reticles produced by such inspection systems. Additional, secondary inaccuracies between the aerial images predicted by inspection systems and those printed by exposure systems may be caused by the fact that such inspection systems form aerial images of a reticle that would be printed in air. For example, conventional aerial imaging reticle inspection systems do not account for variation in an aerial image of a reticle that will be printed in a resist due to refraction of s- and p-polarized light through the resist. For example, most resists have a refractive index that is not 1. In some examples, resists designed for ultraviolet or very ultraviolet applications generally have refractive index values between about 1.4 and 1.8. An average refractive index of such resists may be about 1.7. Therefore, the angles at which the light propagates through the resist may be less oblique that the angles at which the light was projected onto the upper surface of the resist. In other words, a lower NA conditions exists within the resist. Such refraction of the s- and p-polarized light in the resist will alter the aerial image of the reticle that is projected into the resist. In this manner, the aerial image that is projected through the resist is different than the aerial image that is projected into the resist. Consequently, the image of the reticle that is printed in the resist may be different, and in some cases may be substantially different, than the aerial image of the reticle in air. In this manner, aerial images of a reticle produced by a conventional aerial imaging reticle inspection system may differ substantially from an image of the reticle that would be printed in a resist.

Furthermore, conventional aerial imaging reticle inspection systems do not account for variation in an aerial image of a reticle due to transmission of s- and p-polarized light through the resist. For example, bulk absorption in most resists can be described using the Beer-Lambert law, where transmitted dose or intensity through a resist is related to absorption and thickness. As light travels through a resist, the light loses intensity due to absorption of the light by the resist. Therefore, absorption of light by a resist reduces image contrast with increasing depth. In addition, as the thickness of the resist increases, the image contrast will be reduced. In general, image gradients for both s-polarized light and p-polarized light will degrade as the absorption and the thickness of the resist increase. The effects of image contrast degradation should be considered in conjunction with the other factors described herein since absorption of s- or p-polarized light can compound the above effects on the image of a reticle that will be printed in a resist.

Furthermore, light projected onto the detector may not have the same polarization characteristics as light projected by the exposure system onto the wafer. For example, different light sources may emit light having the same wavelength but different polarization characteristics. Therefore, even if the inspection system has the same wavelength of illumination as the exposure system, the illumination of the inspection system may not have the same polarization characteristics as the exposure system. In addition, the light sources of currently available aerial imaging inspection systems are selected without regard to the polarization characteristics of the light emitted by the light sources. Furthermore, some exposure systems have optical components that are used to alter the polarization of the light emitted by the light source before it is projected onto a wafer. Currently available aerial imaging inspection systems, however, do not include any such optical components. As such, currently available aerial imaging inspection systems are not configured to simulate the polarization characteristics of light in the exposure system. Therefore, an aerial image acquired by the inspection system may have different characteristics than an aerial image of the reticle printed by the exposure system. In addition, an aerial image formed by the inspection system and an aerial image printed by a high NA exposure system may be significantly different, even if the NA of the inspection system is approximately equal to the NA of the exposure system.

For at least the above reasons, conventional aerial imaging systems cannot accurately predict how an image of the reticle will be printed in the resist. Such information is most interesting to integrated circuit manufacturers or other people who are going to print images of the reticle into a resist. In addition, such information is becoming increasingly important to the reticle manufacturer. For example, the image of how the reticle will print in the resist can be used to determine which defects on the reticle must be repaired. In one example, only those defects that are shown to print in the resist may be repaired. In contrast, defects that do not undesirably alter the image of the reticle that is printed in the resist may not be repaired. Therefore, the number of defects on the reticle that are repaired can be reduced, which in turn reduces the manufacturing costs for producing the reticle. Since conventional aerial imaging systems do not produce images that accurately predict how the reticle will print in the resist, such images cannot be used to accurately predict which defects should be repaired and which defects do not have to be repaired. In addition, the aerial image acquired by the detector will not accurately simulate the lateral dimensions of features of the reticle as they would be printed by the exposure system. Therefore, an aerial image generated by the inspection system also may not be used to accurately determine if the reticle passes qualification.

FIGS. 3–7 illustrate exemplary embodiments of reticle inspection systems configured to simulate the effects of NA and polarization on aerial images of a reticle. Some embodiments of the reticle inspection systems include a spatial filter configured to simulate the effects of NA and polarization on aerial images of a reticle. Elements of FIGS. 3–7 that may be similarly configured have been indicated with the same reference numerals. However, it is to be understood that elements of different figures that are indicated with the same reference numerals do not have to be similarly configured.

The system may include an optical subsystem coupled to a processor (not shown). The optical subsystem may include an illumination subsystem and a collection subsystem. The illumination subsystem includes light source 38. Light source 38 may be a coherent light source such as a laser. The light source may be configured to emit monochromatic light having a wavelength of about 365 nm, about 248 nm, about 193 nm, about 157 nm, or another ultraviolet wavelength. Alternatively, the light source may be configured to emit light having a range of wavelengths and may be coupled to a spectral filter (not shown). An example of a broadband light source includes, but is not limited to, a He—Xe arc lamp that generates light in the deep ultraviolet wavelength regime. In this manner, the light source and the filter may emit monochromatic light having a wavelength as described above. The light source and the filter may be configured such that different wavelengths of light may be emitted from the light source and the filter depending upon, for example, the type of reticle being inspected or the type of inspection or measurement being performed. In addition, the light source may be configured to emit light continuously or at various time intervals in pulses. The light source, and optionally the spectral filter, are configured to emit light having a wavelength approximately equal to a wavelength of the exposure system, $\lambda_{litho}$.

The illumination subsystem may also include a number of optical components coupled to the light source. For example, light from light source 38 may pass through homogenizer 40. Homogenizer 40 may be configured to reduce speckle of the light from the light source. The illumination subsystem may also include aperture 42. Aperture 42 may be an adjustable numerical aperture. For example, the aperture may be coupled to a control mechanism that may be configured to mechanically alter the aperture depending upon a control signal received from a user or from program instructions received from a program recipe being run on the system. In this manner, the light may have various partial coherence factors, σ. For example, aperture 42 may be altered to adjust a pupil of condenser lens 44. The pupil of the condenser lens controls the coherence of the illumination of the system. As the pupil of the condenser is reduced, coherence of the illumination increases thereby decreasing the value of σ.

The value of σ may be expressed as the ratio of the numerical aperture of the condenser lens to the numerical aperture of the objective lens. Exposure systems may have a value of σ in a range between about 0.3 to about 0.9. The value of σ may be altered depending upon the features being printed onto a specimen or being inspected. For example, a higher value for σ may be used if the reticle includes lines and spaces than if the reticle includes contact holes. Aperture 42 may be altered such that the inspection system has a value of σ between about 0.3 and about 0.9. In particular, the numerical aperture of aperture 42 is adjusted such that the light has a partial coherence factor approximately equal to a partial coherence factor of the exposure system, $\sigma_{litho}$. The control mechanism may also be configured to alter the aperture to provide annular or off-axis illumination. The aperture may also be configured to provide other types of illumination such as quadrapole or dipolar illumination. The aperture may be further configured to alter a shape of the beam of light. For example, the aperture may be a diffraction optical element or an apodization aperture. Therefore, the aperture of the inspection system can be adjusted such that the inspection system has the same type of illumination and the same shape of the light beam as the exposure system.

The illumination subsystem may also include condenser lens 44. Condenser lens 44 may be configured to alter a diameter of the light in the object (reticle) plane to approximately, or greater than, the field of view of the system. Light exiting the condenser lens may illuminate reticle 46 supported upon a stage (not shown). The stage is configured to support the reticle by contacting the reticle proximate outer lateral edges of the reticle. An opening in the stage is provided to allow light from the illumination subsystem to illuminate the reticle. The stage may be configured to move the reticle such that an alignment of the reticle may be altered and such that light may scan across the reticle. Alternatively, the illumination system may include a scanning element (not shown) such as an acousto-optical deflector or a mechanical scanning assembly such that the reticle may remain substantially stationary while the light is scanned across the reticle. The stage may also be configured to move the reticle through focus thereby altering a focus setting of the system. The stage may also be coupled to an autofocusing device (not shown) that is configured to alter a position of the stage thereby altering a position of the reticle to maintain a focus setting of the system during an inspection. Alternatively, an autofocusing device may be coupled to the objective lens to alter a position of the objective lens to maintain the focus setting during an inspection.

The illumination subsystem may also include a number of additional optical components (not shown). For example, the illumination subsystem may also include a telescope configured to alter the beam diameter of the light. In addition, the illumination subsystem may include one or more relay lenses, additional lenses such as a field lens, folding mirrors, additional apertures, and beamsplitters.

Light transmitted by the reticle is collected by objective lens 50. The objective lens is configured to form an aerial image of the reticle. The objective lens may have an NA on the reticle side of the objective lens approximately equal to an NA on the reticle side of the exposure system (i.e., $NA_{litho}/4$). The NA of objective lens 50 on the detector side of the objective lens may be about $NA_{litho}/150$. The NA of objective lens 50 on the detector side, however, may vary and will not affect the accuracy of the aerial image acquired by the detector.

The system of FIG. 3 also includes optical filter 56. Optical filter 56 may be disposed at a back focal plane of objective lens 50, as shown in FIG. 3. In addition, the optical filter may be arranged in any Fourier plane of the objective lens. In some instances, the exit plane of the optical filter may be Fourier-transformed to the image plane or another equivalent plane of the objective lens. In some embodiments, the optical filter and the system may be configured such that the optical filter may be changed depending on the reticle being inspected, characteristics of the exposure system which will print images of the reticle, and/or characteristics of the resist into which images of the reticle will be printed. The optical filter and the system may be configured such that the optical filter may be changed manually or automatically.

Optical filter 56 may be configured to simulate the effects of NA and polarization on aerial images of a reticle. For example, optical filter 56 may be configured to alter the interference between electric fields of p-polarized light in the image plane. In particular, the optical filter may be configured to alter the interference between the electric fields of p-polarized light in the image plane such that the interference is substantially equivalent to the interference between the electric fields of p-polarized light that would exist in an image plane at the numerical aperture on the wafer side of the exposure system. For example, as described in more detail above, as NA increases, the interference between electric fields of p-polarized light in the image plane will decrease. Therefore, in some embodiments, the optical filter may be configured to reduce the interference between electric fields of p-polarized light in the image plane of the inspection system. In other words, the optical filter may be configured to decrease the electric fields of p-polarized light in the image plane at high incidence angle. In this manner, the optical filter may be configured to decrease an overall intensity of the p-polarized light in the image plane. Consequently, the optical subsystem can be configured to simulate the conditions in a high NA exposure system. In particular, the optical subsystem simulates the intensity of p-polarized light that would be projected into a resist by the exposure system at the numerical aperture of the exposure system without necessarily forming an aerial image of the reticle at the numerical aperture of the exposure system.

The optical filter, however, is not configured to alter interference between electric fields of s-polarized light in the image plane since nearly complete interference of the electric fields of s-polarized light will exist regardless of the numerical aperture at which the aerial image is formed. Therefore, the aerial images formed separately with p-polarized light and s-polarized light by the inspection system will be approximately equivalent to the images that would be formed by an exposure system. Since aerial images that are produced by the inspection system are a sum of the separately formed images, the aerial images will be substantially equivalent to aerial images of the reticle that would be formed by an exposure system. For example, an aerial image formed by the inspection system illustrated in FIG. 3 will have approximately the same image contrast as an aerial image of the reticle printed by an exposure system.

In one such embodiment, the optical filter may include a wave retarder. For example, a wave retarder may be configured to delay one of the components of the light transmitted by the reticle without delaying the other component of the light. In the above example, therefore, the wave retarder may delay the p-polarized component of the light transmitted by the reticle. The wave retarder may also have properties that vary as a function of position across the wave retarder. For example, the wave retarder may be configured to delay the p-polarized component of the light depending on position of the light in the aerial image. In particular, the wave retarder may be configured to delay p-polarized components of the light differently depending on the position of the reticle through which the light was transmitted and the angle at which the light will be projected onto the image plane of the optical subsystem. For example, since the largest differences in interference between p-polarized light in an aerial image produced by the optical subsystem and in an image projected into a resist by an exposure system will occur at the most oblique angles, the wave retarder may be configured to at least delay the p-polarized components of the light that will be projected onto the detector at the most oblique angles. Examples of an appropriate wave retarder may include a quarter-wave retarder or a half-wave retarder.

In another such embodiment, the optical filter may be a polarization rotator. A polarization rotator may be configured to rotate the plane of polarization of linearly polarized light by some angle, while maintaining the linear polarization characteristics of the light. In the above example, therefore, the polarization rotator may rotate the plane of polarization of the p-polarized component of the light transmitted by the reticle. The polarization rotator may also have properties that vary as a function of position across the polarization rotator. For example, the polarization rotator may be configured to delay the p-polarized component of the light depending on position of the light in the aerial image as described above. Examples of appropriate polarization rotators may include optically active media, materials exhibiting the Faraday effect, and a twisted nematic liquid crystal.

Optical filter 56 may also be configured to alter an amount of s-polarized light and/or an amount of p-polarized light that is collected by the objective lens. In this manner, the optical filter may alter the intensity of s-polarized light and/or p-polarized light in an aerial image formed by the objective lens. In one embodiment, the optical filter may be configured to reduce the amount of s-polarized light and/or the amount of p-polarized light that is collected by the objective lens. The amount by which the s-polarized light and/or p-polarized light is reduced by the optical filter may vary depending upon characteristics of a resist in which an image of the reticle is to be printed, characteristics of an exposure system, and/or characteristics of the reticle. For example, as described above, the amount of s- and p-polarized light that is reflected from the resist may depend on a number of characteristics of the exposure system (i.e., NA and wavelength) and the reticle (i.e., resolution or pitch of features).

In some embodiments, the amount by which the s-polarized light and/or p-polarized light is reduced by the optical filter may vary depending on properties of a resist. In addition, the amount (and the associated phases) of light reflected and transmitted into the resist will vary depending upon the polarization of the light projected into the resist. The s- and p-components of the reflection coefficient for a resist may be determined from expressions for the Fresnel reflection coefficients, which include variables for the complex reflection coefficients for upper and lower interfaces of the resist, the thickness of the resist, and the complex index of refraction of the resist. Therefore, the s- and p-components of the reflection coefficient for a resist may be used to determine an appropriate optical filter for a reticle exposure system. For example, optical filter 56 may be configured to have s- and p-components of the reflection coefficient that are approximately equal to s- and p-components of the reflection coefficient of the resist. In this manner, the optical filter may be configured to alter the light to simulate reflection and transmission of s- and p-components of the light into a resist. In other words, the amount of s-polarized light and/or the amount of p-polarized light which is reduced by the optical filter may be approximately equal to the amount of s-polarized light and/or the amount of p-polarized light that is reflected from the upper surface of the resist.

In this manner, the optical filter may simulate the dose of s-polarized light and/or p-polarized light that is projected into the resist. Since the objective lens forms an aerial image after such amounts of s-polarized light and/or p-polarized light are reduced by the optical filter, the aerial image formed by the objective lens will be representative of the aerial image that is projected into the resist. In such embodiments, examples of appropriate optical filters include, but are not limited to, a partially anisotropic material (i.e., a partially dichroic material) that can selectively absorb polarized light, two dielectric isotropic materials having a boundary that can selectively reflect polarized light, a partially anisotropic crystal that can selectively refract polarized light and spatially separate polarized light, a wave retarder, a wave retarder in combination with one or more polarizers, and a polarization rotator.

In some embodiments, optical filter 56 may be configured to alter the interference between electric fields of p-polarized light in the image plane in addition to being configured to alter an amount of s-polarized light and/or an amount of p-polarized light that is collected by the objective lens. In such embodiments, the optical filter may include one or more of the appropriate optical filters described above. If the optical filter includes more than one filter, the filters may be disposed at approximately the same location in the optical subsystem or at different locations in the optical subsystem. Furthermore, the filters may be coupled to each other (i.e., mechanically or otherwise such as by an adhesive), but boundaries of the different filters may be defined by an interface or a spacing between the filters. Alternatively, the filters may be separately disposed within the optical subsystem (i.e., by separate mechanical devices). If the optical filter includes only one filter, the filter may include one or more continuous layers (i.e., such that an interface does not exist within the layers). The filter may also include one or more non-continuous or segmented layers. In addition, the properties of the filter may vary as a function of position within the filter. In some embodiments, the properties of the filter may vary in two dimensions (i.e., in the plane of the filter that is perpendicular to the optical axis of the optical subsystem).

Figure 4:
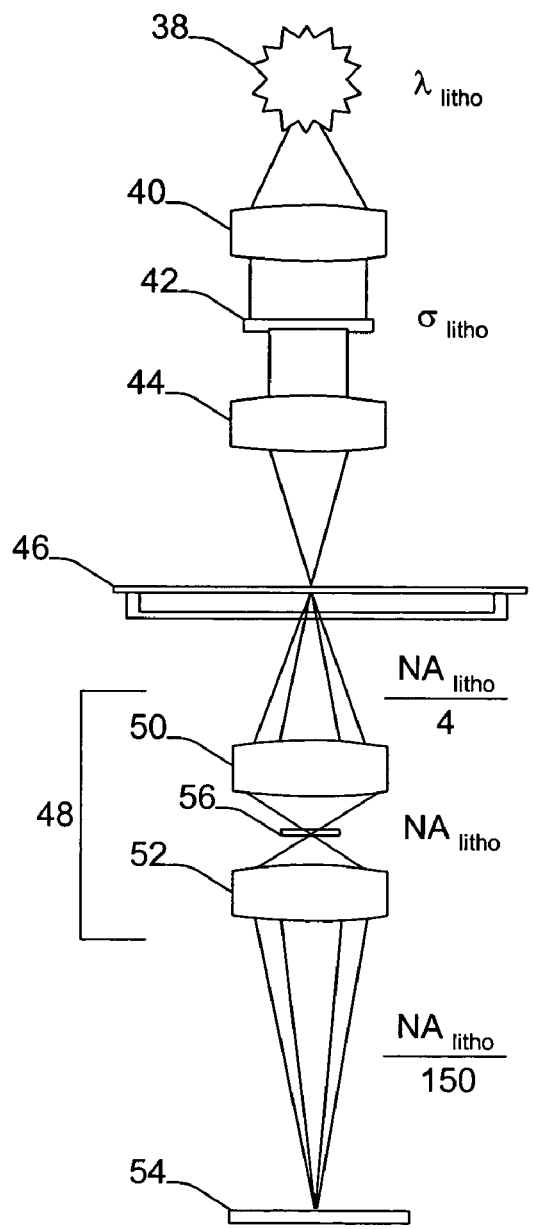

In another embodiment, the optical subsystem includes a spatial filter. Several different configurations for spatial filter 48 are shown in FIGS. 4–7. As shown in FIG. 4, light transmitted by the reticle is collected by spatial filter 48. The spatial filter may be configured to form an aerial image of the reticle at a numerical aperture of greater than about 0.5. Therefore, the spatial filter may form the aerial image of the reticle at a high NA. In some embodiments, the numerical aperture at which the aerial image is formed is approximately equal to a numerical aperture at which an exposure system projects an image of the reticle into a resist, $NA_{litho}$. Examples of such NA are described above. In addition, the spatial filter may have an NA on the reticle side of the spatial filter approximately equal to an NA on the reticle side of the exposure system (i.e., $NA_{litho}/4$). For example, spatial filter 48 includes objective lens 50 configured to collect light transmitted by the reticle. Objective lens 50 has an NA on the reticle side of the objective lens approximately equal to $NA_{litho}/4$. The objective lens also forms an intermediate aerial image of the reticle at a numerical aperture of NA, which may be approximately equal to $NA_{litho}$.

The spatial filter also includes objective lens 52. Objective lens 52 is configured to collect the intermediate aerial image formed by objective lens 50 and to project an aerial image onto detector 54. In some embodiments, objective lens 52 may be configured as a tube lens or a relay lens. The NA of objective lens 52 on the detector side of the objective lens may be about $NA_{litho}/150$. The NA of objective lens 52 on the detector side, however, may vary and will not affect the accuracy of the aerial image acquired by the detector. Objective lens 50 and objective lens 52 may be equivalent objective lenses. In addition, objective lenses 50 and 52 have a 1:1 magnification.

Figure 5:
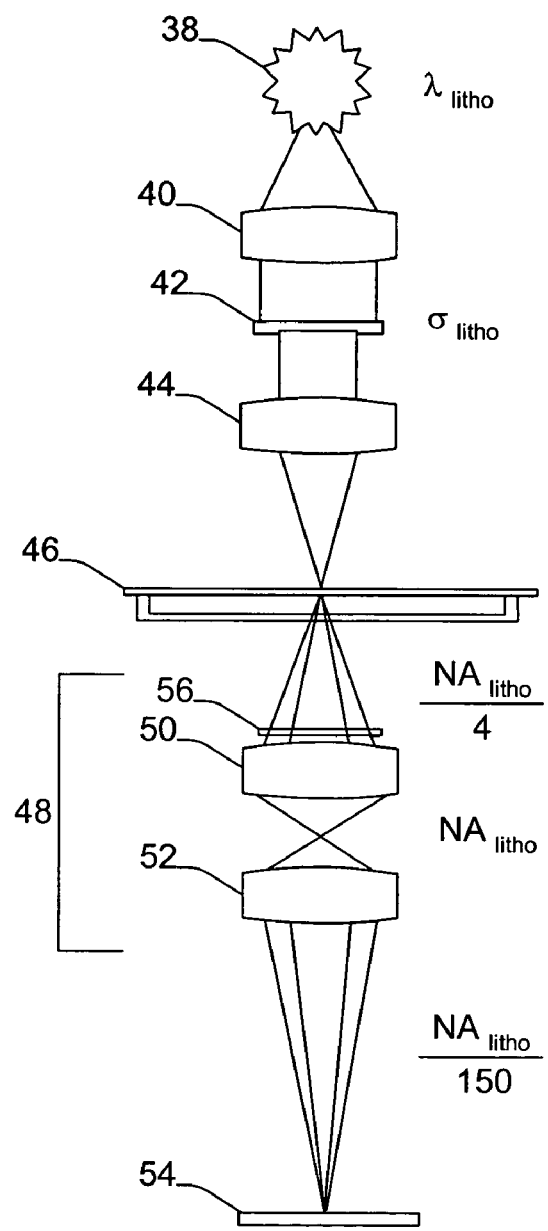

Spatial filter 48 includes optical filter 56. Optical filter 56 may be disposed at a focal point between objective lenses 50 and 52, as shown in FIG. 4. Alternatively, optical filter 56 may be disposed at a back focal plane of objective lens 50, as shown in FIG. 5. In addition, the optical filter may be arranged in any Fourier plane of the spatial filter. In some instances, the exit plane of the optical filter may be disposed in a plane of the spatial filter, which is Fourier-transformed to the image plane or another equivalent plane. The optical filter may be configured to alter the interference between electric fields of p-polarized light in the image plane according to any of the embodiments described above. Such an optical filter may be used if the NA at which objective lens 50 forms the intermediate aerial image of the reticle is not equal to the NA at which the exposure system projects the aerial image into the resist. Optical filter 56 may also be configured to alter an amount of s-polarized light and/or an amount of p-polarized light that is collected by objective lens 50 or objective lens 52 according to any of the embodiments described above. In some embodiments, optical filter 56 may be configured to alter the interference between electric fields of p-polarized light in the image plane in addition to being configured to alter an amount of s-polarized light and/or an amount of p-polarized light that is collected by the objective lens as described above. The optical filter may be further configured as described herein.

Figure 6:
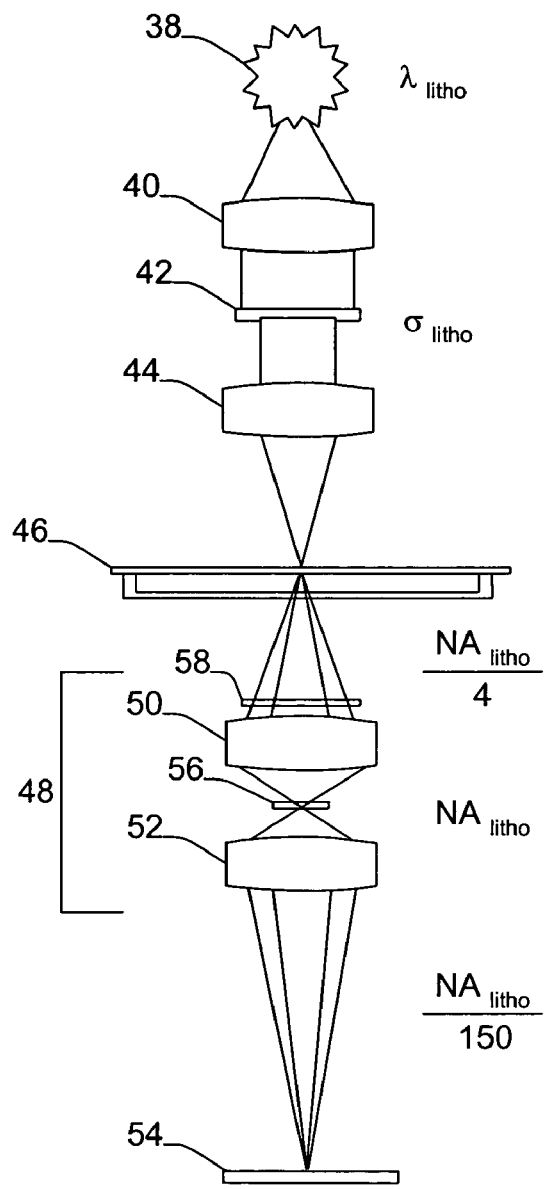
Figure 7:
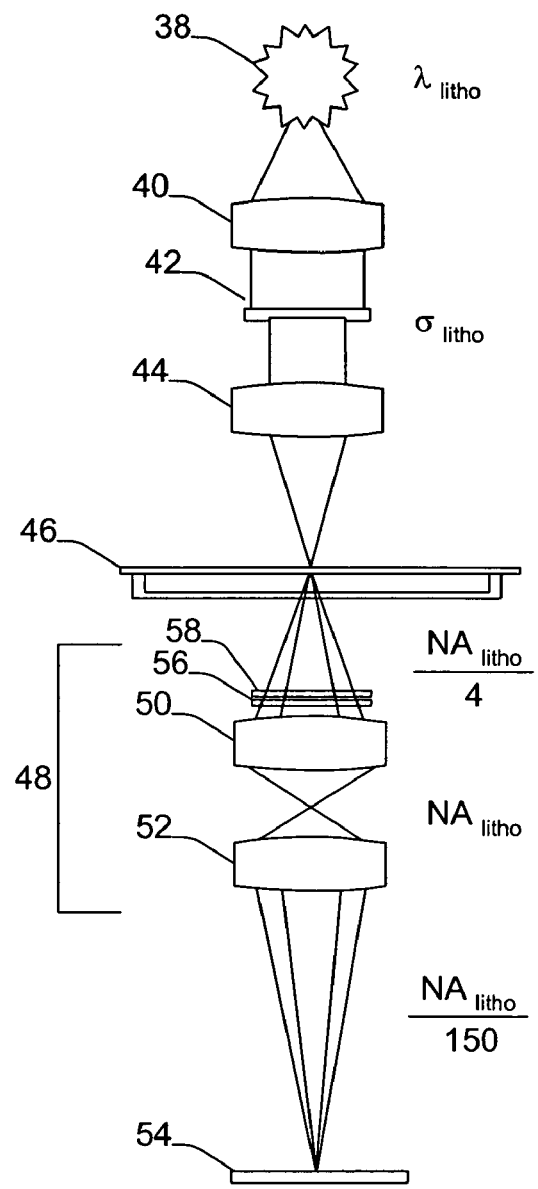

In alternative embodiments, the spatial filter may include more than one optical filter. For example, as shown in FIGS. 6 and 7, the system may include optical filter 56 and optical filter 58. Optical filter 56 may be configured to alter an amount of s-polarized light and/or an amount of p-polarized light that is collected by objective lens 50 or objective lens 52 according to any of the embodiments described above. As shown in FIG. 6, optical filter 56 may be disposed at the image plane between objective lens 50 and objective lens 52. Alternatively, as shown in FIG. 7, optical filter 56 may be disposed at a back focal plane of objective lens 50. In addition, optical filter 56 may be arranged in any Fourier plane of the spatial filter. Optical filter 58 may be configured to alter the interference between electric fields of p-polarized light in the image plane according to any of the embodiments described above. As shown in FIGS. 6 and 7, optical filter 58 may be disposed at a back focal plane of objective lens 50. In addition, the spatial filter and the system may be configured such that optical filter 56 and/or optical filter 58 may be changed depending on the reticle being inspected, characteristics of an exposure system, and/or characteristics of a resist. The spatial filter and the system may be configured such that the optical filter may be changed manually or automatically.

In additional embodiments, spatial filter 48 may also be configured to alter other properties of the light in the aerial image. For example, in one embodiment, spatial filter 48 may be configured to alter the aerial image to simulate filter characteristics of a resist. In some embodiments, such a spatial filter may include optical filter 56 or optical filter 58, as shown in FIGS. 3–7, or an additional optical filter (not shown). The optical filter may be placed in an image plane of the optical subsystem. Transmission characteristics of the optical filter, at an operating wavelength of the exposure system, may be selected to substantially match filter characteristics of the resist, at the operating wavelength. In addition, the transmission characteristics of the optical filter can be selected to approximately match both s- and p-polarization transmission into the resist across the range of angles used in the exposure system illumination. In general, a resist has both real and imaginary parts in its index of refraction. In one example, an index of refraction of a resist may be approximately 1.7 at one wavelength and will vary as a function of the wavelength. Therefore, the transmission characteristics of the optical filter may be selected for s- and p-polarization across the range of illumination angles that the resist would be exposed to by the exposure system to account for the effects that the resist would have on the aerial image. In this manner, an optical system that includes one of the above described spatial filters will produce aerial images of the reticle that may be substantially equivalent to an image of the reticle that will be printed in the resist. Consequently, each of the above described spatial filters increases the accuracy of the aerial images formed by the system.

The optical subsystem may also be configured to alter a polarization of light in the aerial image depending on the polarization characteristics of light projected onto a reticle or resist by an exposure system. In one such embodiment, the optical subsystem may include any optical component that can transmit a selected polarization and that can remove other polarization directions from the light by reflection, refraction, and/or absorption. Examples of such an optical component includes any of the polarizers described above.

In another embodiment, the optical component may be configured to alter the polarization such that the light comprises radially rotating linearly polarized light. For example, if the light is linearly polarized, the optical component may be include facets, each of which is a half-wave plate. The main axes of the facets may be oriented such that the polarization direction is rotated in the direction of the radius of the light beam, or the optical axis. Unpolarized or circularly polarized light may also be converted into radially rotating linearly polarized light. For example, the optical component may be configured to separate the two electric field components. The polarization direction of the undesirable electric field component may be altered such that the light is linearly polarized in the selected direction. Both portions of the separated light may be rotated radially and may be transmitted as a light beam having a substantially homogenous polarization. In this manner, substantially all of the light can be converted to radially rotating linearly polarized light. Examples of optical components that may be used to convert light to radially rotating linearly polarized light are illustrated in U.S. Pat. No. 5,365,371 to Kamon, U.S. Pat. No. 5,559,583 to Tanabe, and U.S. Pat. No. 6,392,800 B2 to Schuster, which are incorporated by reference as if fully set forth herein.

The optical component may also be configured such that the light is radially linear polarized light having a selected polarization direction. In one embodiment, the selected polarization direction is the p-direction. Such radially linear p-polarized light may advantageously simulate the polarization of light projected onto a wafer by a high NA exposure system. For example, when light is projected into a resist at relatively large angles, the light may be reflected at an upper resist boundary. Therefore, a significant portion of light may essentially be wasted. In addition, the light projected at relatively large angles may be reflected at both an upper resist boundary and a lower resist boundary, which may adversely affect the resolution due to standing waves that may form in the resist. The amount of reflection varies depending on the polarization direction and the reflection plane.

In one embodiment, exposure systems may be configured to alter the polarization of light such that if the light was projected into a resist, a substantial portion of the light would not be reflected at one or more resist boundaries. For example, the amount of reflection may be reduced, and even eliminated, if the light projected into the resist has an electrical field oscillating parallel to the incident angle at the brewster angle. In this manner, reflectance of p-polarized light is reduced, and may even be eliminated, when the angle of incidence is the angle of polarization. As such, the amount of light transmitted through the resist may be increased, and the formation of standing waves in the resist may be reduced. Accordingly, high NA exposure systems may be configured to project radially linear p-polarized light to increase the intensity of light projected into the resist by reducing reflection at the upper resist boundary and to reduce the formation of standing waves in the resist. Therefore, the optical component may be configured to alter the polarization of light such that if the light was projected into a resist, a substantial portion of the light would not be reflected at one or more resist boundaries. An optical component, which converts light to radially linear p-polarized light, may, therefore, generate aerial images of a reticle that are substantially equivalent to aerial images of the reticle that would be printed by an exposure system.

In other embodiments, high NA exposure systems may be configured to project light having different polarizations onto a reticle or resist. For example, the polarization of the light projected onto a reticle or resist may vary depending on the type of features that are being printed and to increase a depth of focus of the exposure system. Contact holes, in one example, may be printed more accurately at a polarization different than a polarization used to print other features. Therefore, some high NA exposure systems may include one or more optical components that can alter the polarization of the light projected on a wafer. In some instances, the optical components may vary a polarization across a cross-section of the light. In addition, some optical components may include transmissive and non-transmissive portions. Examples of such optical components are illustrated by U.S. Pat. No. 6,404,482 B1 to Shiraishi, which is incorporated by reference as if fully set forth herein.

The optical component may, therefore, be configured to simulate the polarization of light projected by a specific exposure system or the polarization of light used to print a specific feature. For example, the optical component may vary a polarization across a cross-section of the light. In addition, the optical component may include transmissive and non-transmissive portions. As such, in one embodiment, a reticle inspection system may include an optical component that is configured to alter the polarization of the light such that the polarization is substantially equivalent to a polarization of light projected by an exposure system onto a wafer. In this manner, the reticle inspection system may generate aerial images that are substantially equivalent to images of reticles that would be printed by an exposure system. An appropriate optical component may vary depending upon, for example, the polarization of light projected by the exposure system onto the wafer, the polarization of light emitted by the light source of the inspection system, optical components without phase correction in the inspection system, and polarizing optical components in the inspection system. The optical component may also be configured such that the polarization of light in the aerial image may vary depending on the reticle being inspected.

In some embodiments, the optical component may be arranged external to the spatial filter. For example, a reticle inspection system may include an optical component configured to alter a polarization of light that illuminates the reticle. In such an embodiment, the optical component may be disposed, for example, between aperture 42 and condenser lens 44. Such embodiments may or may not also include an optical filter or a spatial filter, as shown in FIGS. 3–7, or additional optical components. For example, if the inspection system includes optical components without phase correction or polarizing optical components, additional optical components may be configured to re-adjust the polarization of the light in the aerial image.

Each of the embodiments of the optical subsystem illustrated in FIGS. 3–7 may also be configured to correct for radiometric differences between the optical subsystem and the exposure system. A radiometric correction is a geometrical correction that effectively applies an apodization function in the pupil plane of the image. This correction is a function of the magnification ratio of the image. As described by Thomas Pistor, in "Electromagnetic Simulation and Modeling with Applications in Lithography," Ph.D. Dissertation in Electrical Engineering and Computer Sciences, Graduate Division of the University of California, Berkeley, 2001, page 56, the radiometric correction factor $R(k_{out,xy}^2)$ is a consequence of an extension of scalar diffraction theory for imaging in a projection lens where the paraxial approximation is not made. The radiometric correction factor takes the following form:

$$R(k_{out,xy}^2) = \left( \frac{1 - \frac{k_{out,xy}^2}{M^2 k^2}}{1 - \frac{k_{out,xy}^2}{k^2}} \right)^{1/4}$$

where, M is the optical reduction of the projection optic. Therefore, an inspection system, which has a very large magnification ratio (i.e., on the order of about 100 to about 300) compared to an exposure system, which has a magnification ratio of about 0.2 to about 0.25, can be corrected radiometrically to increase the accuracy of the inspection system.

In one such embodiment, the optical subsystem may include an optical component such as a pair of optical elements with aspheric surfaces that distributes the dose of an input beam with one intensity profile to create an output beam having a different intensity profile. The optical component may be disposed at a pupil plane of the image formed by the optical subsystem. In an alternative embodiment, the processor may be configured to alter the aerial image using an apodization function or another modeling function to correct the aerial image for radiometric differences between the optical subsystem and the exposure system. Many such functions are known in the art.

The optical subsystem may, therefore, be configured to simulate exposure conditions of an exposure system and interactions between a resist and light projected into the resist at the exposure conditions. For example, the optical subsystem is configured to produce an aerial image of a reticle by simulating dose as a function of position that would be projected into a resist by an exposure system. As described above, the optical subsystem is configured to alter interference of electric fields of p-polarized light at an image plane of the optical subsystem such that the interference is approximately equivalent to an interference of the electric fields of the p-polarized light at an image plane of the exposure system. In some embodiments, the optical subsystem is configured to form the aerial image at a numerical aperture approximately equal to a numerical aperture on a wafer side of the exposure system. In addition, the optical subsystem may be configured to alter the light to simulate reflection and transmission of s- and p-components of the light by the resist. In this manner, aerial images produced by the optical subsystem are substantially equivalent to images of the reticle that would be projected into the resist by the exposure system.

The optical subsystem may also be configured to further increase the accuracy of the aerial images. For example, the optical subsystem may also be configured to alter a polarization of light in the aerial image such that the polarization is substantially equivalent to a polarization of light projected by an exposure system into a resist. In some embodiments, the optical subsystem may also be configured to alter the light to simulate refraction of the light in the resist. In addition, or alternatively, the optical subsystem may be configured to alter the light to simulate transmission of the light in the resist. In this manner, an aerial image projected by the optical subsystem onto a detector is substantially equivalent to an image of the reticle that would be printed in the resist by the exposure system.

The processor may be configured to control one or more components of the system. For example, a processor may be coupled to and configured to control components of the system such as light source 38, aperture 42, the stage, and detector 54. In this manner, the processor may alter a parameter of various components of the system to set the exposure conditions under which the reticle is inspected. The exposure conditions include, but are not limited to, wavelength of illumination, coherence of illumination, shape of the beam of illumination, numerical aperture at which an aerial image is formed, polarization characteristics of light projected onto the reticle, and focus settings. The exposure conditions may be selected to be substantially equivalent to exposure conditions used by an exposure system to print an image of the reticle. For example, in one embodiment, the spatial filter is configured to form an aerial image of the reticle at a numerical aperture approximately equal to a numerical aperture at which an exposure system projects an image into a resist. In addition, an optical component may also be configured to alter polarization characteristics of light projected onto the reticle such that the polarization characteristics are substantially equivalent to polarization characteristics of light projected by the exposure system onto the reticle. Therefore, an aerial image formed by the system is substantially equivalent to an image of the reticle that would be projected into a resist by the exposure system under the exposure conditions.

In each of the embodiments illustrated in FIGS. 3–7, detector 54 is configured to acquire the aerial image of the reticle. The detector should be sensitive to at least one of the wavelengths of light described above. The detector, however, may also be sensitive to a range of wavelengths in the deep ultraviolet regime in addition to wavelengths in other regimes. The detector may include, for example, a charge-coupled device (CCD) camera or a time delay integration (TDI) camera. The detector may also have a one-dimensional or two-dimensional array of pixels. The detector may have a focus setting approximately equal to a focus setting of an exposure system. Images of the reticle at different focus settings may be formed by forming a plurality of images of the reticle and altering the focus setting of the detector after each image is formed.

The processor may be configured to receive image data from detector 54 representative of an aerial image of a reticle. The processor may also be configured to perform a number of functions on the image data such as, but not limited to, altering the data to reduce the effects of distortion, alignment error, illumination non-uniformities, and/or detector non-uniformities. In addition, the processor may also be configured to detect defects on the reticle from the image data. For example, the processor may compare an aerial image formed using image data from the detector to a reference image stored in a database. Comparing an image of a reticle generated by an inspection system to a reference image is commonly referred to as die-to-database (die: database) inspection.

As described above, the aerial image acquired by the detector is substantially equivalent to an image of the reticle that would be printed by an exposure system. In one embodiment, the reference image is substantially equivalent to an image of the reticle that would be printed by an exposure system if the reticle did not include any defects. Therefore, the processor will detect very few nuisance defects. As used herein, the term "nuisance defects" generally refers to differences between the aerial image and the reference image, which are caused by marginalities in the system (or the inspection method) or the processor (or the detection method) not by actual defects. In this manner, a substantial portion of the defects that are detected on the reticle using the aerial image are defects that would be printed by an exposure system.

In further embodiments, the processor may compare an aerial image of a portion of the reticle to an aerial image of another portion of the reticle. Such inspection is commonly referred to as die-to-die (die:die) inspection. Either comparison may involve comparing a number of properties of the aerial image to the reference image such as intensity, phase, feature edge position, a dimension of the feature, and an area of the feature. Alternatively, the processor may send the image data to a different processor (not shown) configured to generate the aerial image and to detect defects on the reticle using the image data after the functions described above have been performed. Examples of appropriate processors include, but are not limited to, a Silicon Graphics 0-200 computer available from Silicon Graphics, Mountain View, Calif., an HP735 workstation available from Hewlett Packard, Palo Alto, Calif., and a Sun SPARC or Sun ULTRASPARC system available from Sun Microsystems, Sunnyvale, Calif.

As described above, the aerial image acquired by the detector may be substantially equivalent to an image of the reticle that would be printed in a resist. In one embodiment, the reference image is substantially equivalent to an image of the reticle that would be printed in the resist if the reticle did not include any defects. Therefore, the processor will defect very few nuisance defects, and a substantial portion of the defects that are detected on the reticle using the aerial image are defects that would be printed in the resist. The aerial image may also be used to analyze various properties of an image of the reticle that would be printed in a resist. For example, the aerial image may be used to determine various properties of features that would be printed in a resist such as linewidth, diameter, height and profile characteristics such as corner rounding, top rounding, roughness, and sidewall angle.

In another embodiment, the reference image may be substantially equivalent to an image of the reticle that if printed in the resist could be used to produce a selected pattern in the resist. For example, the selected pattern may be a pattern formed in the resist after development or etch of the resist, which is selected by a semiconductor manufacturer. The semiconductor manufacturer may select such a pattern based on characteristics and features of devices that are to be formed using the patterned resist as a mask. For example, the patterned resist may be used as a mask for processes such as ion implantation and etch of a material underlying the resist such as dielectric and conductive materials. Therefore, the pattern selected by the semiconductor manufacturer may be used to determine the aerial image that could be used to produce the selected pattern in the resist. Such an aerial image may be substantially different than the layout of the reticle.

Models that can be used to determine a patterned resist that would be formed by an aerial image and an aerial image that could be used to produce a selected patterned resist are known in the art. Such models may use parameters of an aerial image, a resist, and a litho process (i.e., post exposure bake parameters and develop parameters) to generate a pattern that may be formed in the resist with the aerial image. If the pattern selected by the semiconductor manufacturer is an etched resist, such models may also use parameters of an etch process to generate a pattern that would be formed in the resist with the aerial image.

In this manner, a comparison of an aerial image generated by the reticle inspection system and a reference image generated from a selected pattern may be used to detect defects on the reticle that would produce defects in the patterned resist. As such, the detected defects may include defects that are meaningful to the semiconductor manufacturer. In addition, defects that are not meaningful to the semiconductor manufacturer may not be detected thereby reducing the detection of nuisance defects and reducing the complexity of analyzing the detected defects.

The system may also include other optical components. In one embodiment, light source 38, or light source 38 and an additional light source (not shown), may be configured to illuminate both sides of the reticle. The system may also be configured to detect light reflected and transmitted by the reticle. Light reflected by the reticle may pass through the same optical components of the collection subsystem as the light transmitted by the reticle. For example, light reflected by the reticle may pass through spatial filter 48. The light reflected from the reticle may be detected by detector 54. In this manner, the light reflected from the reticle and the light transmitted by the reticle may be detected sequentially. Alternatively, the system may include an additional detector (not shown) that may be dedicated to detecting the light reflected from the reticle. As such, the optical subsystem may detect light reflected from the reticle and light transmitted by the reticle substantially simultaneously.

The systems described herein may also be configured to focus light from the light sources to a plurality of spatially separated spots on the reticle. The system may be further configured to detect light transmitted or reflected from the plurality of spots. Such a system may be configured as described and illustrated in U.S. patent application Ser. No. 11/439,621 entitled "Multiple Beam Inspection Apparatus and Method," by Kvamme et al., which is incorporated by reference as if fully set forth herein. The systems described herein may be further configured as illustrated and described by Kvamme et al.

The system may also include a number of optical components arranged to form a collection subsystem in combination with spatial filter 48 and detector 54. For example, the collection subsystem may include a magnification lens (not shown). The magnification lens may be positioned between spatial filter 48 and detector 54. In addition, the system may include more than one detector. Light from spatial filter 48 may be directed to a beamsplitter. The beamsplitter may be configured to direct the light to multiple detectors. Each of the detectors may have a different focus setting. In this manner, the detectors may form images of the reticle at different focus settings substantially simultaneously. For example, one detector may be substantially in focus, and two other detectors may be out of focus in opposite directions with respect to the in focus condition. The focus settings for each of the detectors may also be altered by altering a position of the detectors using, for example, a mechanical device. In addition, the system may include any number of such detectors depending on the mechanical or physical constraints of the system.

The system may include a number of other components that are not shown in FIGS. 3–7. For example, the system may include a load module, an alignment module, a handler such as a robotic transfer arm, and an environmental control module and may include any such components known in the art.

As described above, various parameters of the optical components may be altered. Therefore, the system may be used to form a plurality of aerial images of the reticle using different exposure conditions of an exposure system. For example, a mechanical device may be used to alter a position of the detector to alter a focus setting of the detector. The processor may be coupled to the mechanical device and may be configured to control the mechanical device to alter a position of the detector.

A process window for the exposure system may be determined using the aerial images. The process window may include exposure conditions under which aerial images of the reticle may be printed without defects or with defects within process control limitations. The process window may also include a range of values for parameters such as focus and dose settings of the exposure system at which the exposure system will print various features of the reticle onto a specimen within process control limitations. The process control limitations may include a range of values for various properties of the printed features such as linewidth, diameter, height and profile characteristics such as corner rounding, top rounding, roughness, and sidewall angle. In this manner, the process window may be determined by analyzing properties of printed features of the aerial images and determining the exposure conditions that yielded printed features having properties within process control limitations. A process window of the exposure system may also be determined using the aerial image and a software program such as Klarity ProDATA commercially available from KLA-Tencor.

After defects have been detected on the reticle, the defects are typically reviewed. Reviewing defects may include performing one or more functions on the image data. The one or more functions may include, but are not limited to, determining a property of a defect such as a dimension, assessing printability of the defect, determining a performance characteristic of an exposure system such as a process window, classifying the defect, and determining a root cause of the defect. The one or more functions that are performed during review may vary, for example, depending upon program instructions received from a user. Defect review may be performed manually by the user or automatically by the system.

The one or more functions performed during defect review may also include generating a two-dimensional or three-dimensional map of the reticle. In one embodiment, the processor may be configured to obtain position data of the stage from an interferometer coupled to the stage. Therefore, the processor may associate image data from the detector with a two-dimensional position on the reticle. The map may include a plot of the defects detected on the reticle as a function of spatial position on the reticle.

The map may include only a subset of the detected defects or all of the detected defects. For example, a map may be generated that includes only defects that were detected in critical regions on the reticle. Alternatively, the map may include only defects having a lateral dimension within a predetermined range, a particular classification, or a particular cause. Generating a map of only a subset of defects may be used to provide only the defect information about which a user cares to view. For example, a user may only want to see defects in critical areas, having a lateral dimension greater than about 5 mm, classified as missing chrome, and/or caused by incomplete resist coverage during lithography. The processor may be configured to select such defects from all of the detected defects and generate a two- or three-dimensional map of the defects.

In addition, or alternatively, the map may include properties of printed features as a function of spatial position on the reticle. The properties may include, for example, lateral dimension of features on the reticle. The map may also include some type of indication for different ranges of the property. The indicia may include color coding, flags, or any other such indicia known in the art. In this manner, the map may illustrate variations in a plot of a property of printed features of the reticle as a function of spatial position of the reticle.

The image data may be analyzed, organized and displayed by any suitable means. For example, the data could be grouped across the reticle as a continuous function of spatial position, binned by spatial ranges, binned by exposure system field, by x-y position (or range of x-y positions, such as on a grid), by nearest die, and/or other suitable methods. The variation in image data may be reported by standard deviation from a mean value, the range of values, and/or any other suitable statistical method. The position data may also be received by another controller device of the system. The controller device may use the position data to control one or more parameters of other components of the system such as timing of the light source and the detectors.

The extent of the within reticle variation (such as the range, standard deviation, and the like) may also be analyzed as a function of process conditions. For example, the within reticle standard deviation of the measured lateral dimension may be analyzed as a function of variation in one or more process conditions such as develop time, exposure conditions, resist thickness, post exposure bake time and/or temperature, pre-exposure bake time and/or temperature, etch parameters, and cleaning parameters. It may also, or instead, be grouped, reported and/or analyzed as a function of within reticle variation in one or more of such processing conditions.

The processor may also be configured to output the results of the inspection procedure to a number of modules such as a display medium, a printer, a storage medium, a database, and a fab database. A fab database may include information related to any of the processes performed in a fab such as tool history, wafer history, and reticle history. A fab database may also include any set of data suitable for use in an overall fab management system. An example of such a system is illustrated in PCT Publication No. WO 99/59200 to Lamey et al., which is incorporated by reference as if fully set forth herein.

The defects detected as described herein may be used to determine if the reticle meets qualification criteria. Qualification is a final inspection step that is performed after reticle manufacturing is complete and before the reticle is used to fabricate integrated circuits. Various properties of the detected defects may be used to determine if the reticle meets qualification criteria. For example, the number, dimensions, locations, and/or designations of region or location (which may be determined as described herein) may be compared to predetermined ranges of the various properties set out in the qualification criteria. If the reticle does not pass qualification, the reticle may be repaired. The reticle may be re-inspected after repair.

Inspection may also be performed periodically after the reticle has been released for semiconductor fabrication to determine if the reticle no longer meets qualification standards. For example, the reticle may be damaged after release by accumulation of particles or other material on the reticle, pellicle damage, and damage caused by electrostatic discharge. Such damage may be sufficient to cause the reticle to fail to meet qualification standards. Example of systems and methods for inspecting a reticle subsequent to qualification are illustrated in U.S. patent application Ser. No. 08/993,107 entitled "Method for Inspecting a Reticle," to Bareket et al., which is incorporated by reference as if fully set forth herein. The systems and methods described herein may be further configured and may include additional steps, respectively, as illustrated and described by Bareket et al.

Additional examples of methods and systems for detecting defects on a surface of a reticle or another specimen are illustrated in U.S. Pat. No. 4,247,203 to Levy et al., U.S. Pat. No. 4,347,001 to Levy et al., U.S. Pat. No. 4,378,159 to Galbraith, U.S. Pat. No. 4,448,532 to Joseph et al., U.S. Pat. No. 4,532,650 to Wihl et al., U.S. Pat. No. 4,555,798 to Broadbent, Jr. et al., U.S. Pat. No. 4,579,455 to Levy et al., U.S. Pat. No. 4,633,504 to Wihl, U.S. Pat. No. 4,641,967 to Pecen, U.S. Pat. No. 4,758,094 to Wihl et al., U.S. Pat. No. 4,766,324 to Saadat et al., U.S. Pat. No. 4,805,123 to Specht et al., U.S. Pat. No. 4,845,558 to Tsai et al., U.S. Pat. No. 4,877,326 to Chadwick et al., U.S. Pat. No. 4,926,489 to Danielson et al., U.S. Pat. No. 5,189,481 to Jann et al., U.S. Pat. No. 5,563,702 to Emery et al., U.S. Pat. No. 5,572,598 to Wihl et al., U.S. Pat. No. 5,737,072 to Emery et al., U.S. Pat. No. 5,889,593 to Bareket, U.S. Pat. No. 6,052,478 to Wihl et al., U.S. Pat. No. 6,076,465 to Vacca et al., U.S. Pat. No. 6,122,046 to Almogy, U.S. Pat. No. 6,137,570 to Chuang et al., U.S. Pat. No. 6,141,038 to Young et al., U.S. Pat. No. 6,175,645 to Elyasaf et al., U.S. Pat. No. 6,282,309 to Emery, and U.S. Pat. No. 6,363,166 to Wihl et al. to all of which are incorporated by reference as if fully set forth herein. Additional examples of defect inspection methods and apparatuses are illustrated in PCT Application Nos. WO 99/38002 to Elyasaf et al. and WO 00/70332 to Lehan, which are incorporated by reference as if fully set forth herein. Further examples of defect inspection methods and apparatuses are illustrated in European Patent Application Nos. EP 1 061 358 A2 to Dotan, EP 1 061 571 A2 to Ben-Porath, and EP 1 069 609 A2 to Harvey et al., which are incorporated by reference as if fully set forth herein. As such, the embodiments described above may also include features of any of the systems and methods illustrated in all of the patents which have been incorporated by reference herein.

Further modifications and alternative embodiments of various aspects of the invention may be apparent to those skilled in the art in view of this description. For example, methods and systems for inspecting a reticle are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A reticle inspection system, comprising an optical subsystem configured to produce an aerial image of a reticle by simulating dose as a function of position that would be projected into a resist by an exposure system such that the aerial image is substantially equivalent to an image of the reticle that would be projected into the resist by the exposure system.

2. The system of claim 1, wherein said simulating comprises altering the aerial image to correct for differences between a numerical aperture at which the exposure system projects the image into the resist and a numerical aperture at which the optical subsystem produces the aerial image.

3. The system of claim 1, wherein the optical subsystem comprises a detector configured to produce the aerial image, and wherein said simulating comprises forming an intermediate aerial image at a numerical aperture approximately equal to a numerical aperture at which the exposure system projects the image into the resist and projecting the intermediate aerial image onto the detector.

4. The system of claim 1, wherein said simulating comprises altering interference of electric fields of p-polarized light at an image plane of the optical subsystem such that the interference is approximately equivalent to an interference of the electric fields of the p-polarized light at an image plane of the exposure system.

5. The system of claim 1, wherein said simulating comprises altering an intensity of p-polarized light in the aerial image such that the intensity is approximately equal to an intensity of the p-polarized light in the image projected into the resist by the exposure system.

6. The system of claim 1, wherein said simulating comprises altering an intensity of s-polarized light in the aerial image such that the intensity is approximately equal to an intensity of the s-polarized light in the image projected into the resist by the exposure system.

7. The system of claim 1, wherein said simulating comprises altering the aerial image to simulate refraction and transmission of p-polarized light and s-polarized light in the resist.

8. The system of claim 1, wherein the optical subsystem comprises an optical filter placed in an image plane of the optical subsystem, wherein transmission characteristics of the optical filter, at an operating wavelength of the exposure system, are selected to substantially match filter characteristics of the resist, at the operating wavelength.

9. The system of claim 1, wherein the optical subsystem comprises a spatial filter, and wherein the spatial filter comprises two equivalent objective lenses and an optical filter disposed at a focal point between the two equivalent objective lenses.

10. The system of claim 1, wherein the optical subsystem comprises a spatial filter and a detector, and wherein the spatial filter comprises a first equivalent objective lens configured to form an intermediate aerial image of the reticle, an optical filter disposed at a back focal plane of the first equivalent objective lens, and a second equivalent objective lens configured to project the intermediate aerial image onto the detector.

11. The system of claim 1, wherein the optical subsystem comprises an optical filter configured to alter polarization characteristics of light in the aerial image such that the polarization characteristics are substantially equivalent to polarization characteristics of light in the image projected into the resist by the exposure system.

12. The system of claim 1, wherein the optical subsystem is further configured to illuminate the reticle with light having polarization characteristics substantially equivalent to polarization characteristics of light projected onto the reticle by the exposure system.

13. The system of claim 12, wherein the optical subsystem comprises an optical filter placed in an image plane of the optical subsystem, wherein transmission characteristics of the optical filter, at an operating wavelength of the exposure system, are selected to substantially match filter characteristics of the resist, at the operating wavelength.

14. The system of claim 1, further comprising a processor configured to detect defects on the reticle by analyzing the aerial image, wherein a substantial portion of the defects comprises defects that would be printed by the exposure system.

15. A reticle inspection system, comprising an optical subsystem configured to alter one or more properties of light transmitted by a reticle and to project the light onto a detector configured to produce an aerial image of the reticle.

16. The system of claim 15, wherein the one or more properties comprise interference of electric fields of p-polarized light at an image plane of the optical subsystem.

17. The system of claim 15, wherein the one or more properties comprise an intensity of p-polarized light transmitted by the reticle.

18. The system of claim 15, wherein the one or more properties comprise an intensity of s-polarized light transmitted by the reticle.

19. A reticle inspection system, comprising an optical subsystem configured to form an intermediate aerial image of a reticle at a numerical aperture approximately equal to a numerical aperture at which an exposure system projects an image of the reticle into a resist and to project the intermediate aerial image onto a detector configured to produce an aerial image of the reticle.

20. The system of claim 19, wherein the optical subsystem comprises an optical filter configured to alter an intensity of s-polarized light in the intermediate aerial image such that the intensity is approximately equivalent to an intensity of the s-polarized light in the image projected into the resist by the exposure system.

21. The system of claim 19, wherein the optical subsystem comprises an optical filter configured to alter an intensity of p-polarized light in the intermediate aerial image such that the intensity is approximately equivalent to an intensity of the p-polarized light in the image projected into the resist by the exposure system.

* * * * *